(12) United States Patent
Hamersma et al.

(10) Patent No.: US 12,085,915 B2
(45) Date of Patent: *Sep. 10, 2024

(54) SAFETY IN DYNAMIC 3D HEALTHCARE ENVIRONMENT

(71) Applicant: KONINKLIJKE PHILIPS N.V., Eindhoven (NL)

(72) Inventors: Ivo Willem Josef Hamersma, Eindhoven (NL); Johan Juliana Dries, Arendonk (BE); Markus Johannes Harmen Den Hartog, Eindhoven (NL); Yannick Morvan, Veldhoven (NL); Marinus Jacobus Gerardus Van De Molengraft, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/750,588

(22) Filed: May 23, 2022

(65) Prior Publication Data

US 2022/0283563 A1 Sep. 8, 2022

Related U.S. Application Data (63) Continuation of application No. 14/007,654, filed as application No. PCT/IB2012/051550 on Mar. 30, 2012, now Pat. No. 11,372,391.

(30) Foreign Application Priority Data

Apr. 6, 2011 (EP) .................................. 11305396
Apr. 27, 2011 (EP) .................................. 11305493

(51) Int. Cl.
G05B 19/4061 (2006.01)
A61B 6/00 (2006.01)
(Continued)

(52) U.S. Cl.
CPC .......... G05B 19/4061 (2013.01); A61B 6/102 (2013.01); A61B 6/547 (2013.01);
(Continued)

(58) Field of Classification Search
CPC .............. G05B 19/4061; G05B 19/406; G05B 2219/37567; G05B 2219/39082; H04N 7/183
See application file for complete search history.

(56) References Cited

U.S. PATENT DOCUMENTS

| 4,578,757 A | 3/1986 | Stark |
| 5,050,204 A * | 9/1991 | Siczek ................. A61B 6/4464 378/197 |

(Continued)

FOREIGN PATENT DOCUMENTS

| EP | 1717757 A1 | 11/2006 |
| WO | 201042689 A2 | 4/2010 |
| WO | 2010150148 A1 | 12/2010 |

OTHER PUBLICATIONS

Maeda et al. "Easy Robot Programming for Industrial Manipulators by Manual Volume Sweeping" (Year: 2008).*

(Continued)

*Primary Examiner* — Kathleen V Nguyen (57) ABSTRACT

The present invention relates to safety in a dynamic 3D healthcare environment. The invention in particular relates to a medical safety-system for dynamic 3D healthcare environments, a medical examination system with motorized equipment, an image acquisition arrangement, and a method for providing safe movements in dynamic 3D healthcare environments. In order to provide improved safety in dynamic 3D healthcare environments with a facilitated adaptability, a medical safety-system (10) for dynamic 3D healthcare environments is provided, comprising a detection system (12), a processing unit (14), and an inter- (Continued)

face unit (16). The detection system comprises at least one sensor arrangement (18) adapted to provide depth information of at least a part of an observed scene (22). The processing unit comprises a correlation unit (24) adapted to correlate the depth information. The processing unit comprises a generation unit (26) adapted to generate a 3D free space model (32). The interface unit is adapted to provide the 3D free space model.

22 Claims, 7 Drawing Sheets

(51) Int. Cl.
  *A61B 6/10* (2006.01)
  *B25J 9/16* (2006.01)
  *G05B 19/406* (2006.01)
  *G06T 19/00* (2011.01)
  *H04N 7/18* (2006.01)
(52) U.S. Cl.
  CPC .......... *B25J 9/1666* (2013.01); *G05B 19/406* (2013.01); *G06T 19/00* (2013.01); *H04N 7/183* (2013.01); *G05B 2219/37567* (2013.01); *G05B 2219/39082* (2013.01); *G05B 2219/39091* (2013.01); *G05B 2219/40607* (2013.01); *G05B 2219/45117* (2013.01); *G06T 2210/21* (2013.01); *G06T 2210/41* (2013.01)

(56) References Cited

U.S. PATENT DOCUMENTS

| | | | |
|---|---|---|---|
| 5,485,502 A | 1/1996 | Hinton | |
| 5,513,299 A | 4/1996 | Terasaki | |
| 6,272,368 B1 | 8/2001 | Alexandrescu | |
| 7,149,262 B1* | 12/2006 | Nayar | G06T 3/4015 375/341 |
| 7,372,977 B2 | 5/2008 | Fujimura | |
| 7,590,262 B2 | 9/2009 | Fujimura | |
| 2005/0102166 A1 | 5/2005 | Tohma | |
| 2007/0024614 A1* | 2/2007 | Tam | H04N 13/282 348/E13.02 |
| 2007/0124024 A1 | 5/2007 | Okamoto | |
| 2008/0033410 A1 | 2/2008 | Rastegar | |
| 2008/0100614 A1 | 5/2008 | Augst | |
| 2008/0150965 A1 | 6/2008 | Bischoff | |
| 2009/0043440 A1 | 2/2009 | Matsukawa | |
| 2010/0185327 A1 | 7/2010 | Nakajima | |
| 2012/0182392 A1* | 7/2012 | Kearns | B25J 19/023 348/46 |
| 2012/0194517 A1* | 8/2012 | Izadi | G06F 3/011 345/420 |

OTHER PUBLICATIONS

Maeda et al, "Easy Robot Programming for Industrial Manipulators by Manual Volume Sweeping", 2008.

Fischer, M. et al. "3D Collision Detection for Industrial Robots and Unknown Obstacles using Multiple Depth Images", German Workshop on Robotics—GWR 2009, June 9-10, Braunschweig, Germany.

Humenberger, M. et al. "A fast stereo matching algorithm suitable for embedded real-time systems", Computer Vision and Image Understanding (2010), Vienna, Austria.

Wulf, O. et al. "Fast 3D Scanning Methods for Laser Measurement Systems", Proceedings of the International Conference on Control Systems and Computer Science, vol. 1 (Jul. 2003), pp. 312-317.

Kolb, A. et al. "ToF-Sensors: New Dimensions for Realism and Interactivity", Computer Vision and Pattern Recognition Workshops 2008. Computer Society Conference on Jun. 23-28, 2008, Anchorage, AK.

Chen, S.Y. et al. "Vision Processing for Realtime 3_D Data Acquisition Based on Coded Structured Light", IEEE Transactions on Image Processing, vol. 17, No. 2, Feb. 2008.

* cited by examiner

SAFETY IN DYNAMIC 3D HEALTHCARE ENVIRONMENT

CROSS-REFERENCE TO PRIOR APPLICATIONS

This application is a Continuation of U.S. application Ser. No. 14/007,654, filed Sep. 26, 2013, which is the U.S. National Phase application under 35 U.S.C. § 371 of International Application No. PCT/IB2012/051550, filed on Mar. 30, 2012, which claims the benefit of European Patent Application No. 11305493.6, filed Apr. 27, 2011 and European Patent Application No. 11305396.1, filed on Apr. 6, 2011. These applications are hereby incorporated by reference herein.

FIELD OF THE INVENTION

The present invention relates to safety in dynamic 3D healthcare environments. The invention in particular relates to a medical safety-system for dynamic 3D healthcare environments, a medical examination system with motorized equipment, an image acquisition arrangement, a method for providing safe movements in dynamic 3D healthcare environments, a computer program element and a computer readable medium.

BACKGROUND OF THE INVENTION

In dynamic 3D healthcare environments, a collision of moving parts with other moving parts or with fixedly arranged, or still standing parts, must be avoided to prevent damages and malfunctioning of the system. Therefore, collision detection or collision warning systems are provided to detect a possible collision situation and to provide the possibility to stop the present movement. For example, U.S. Pat. No. 4,578,757 describes a device for prevention of collision between a patient table and an X-ray imaging system in form of a movable C-arm. Another possibility to prevent or detect collisions are sensors provided on moving parts, which give a warning signal in the case of touching another element in order to be able to stop current movement.

SUMMARY OF THE INVENTION

It has been shown that collision sensors often limit the possible movement speed for dynamic 3D healthcare environments. As a further disadvantage, the adaptability of dynamic 3D healthcare environments can be limited or requires a cumbersome adaption of a respective collision prevention system.

Hence, there is a need to provide improved safety in dynamic 3D healthcare environments with a facilitated adaptability.

The object of the present invention is solved by the subject-matter of the independent claims, wherein further embodiments are incorporated in the dependent claims.

It should be noted that the following described aspects of the invention apply also for the medical safety-system for dynamic 3D healthcare environments, the medical examination system with motorized equipment, the method for providing safe movements in dynamic 3D healthcare environments, the computer program element and the computer-readable medium.

According to an aspect of the invention, a medical safety-system for dynamic 3D healthcare environments is provided, comprising a detection system, a processing unit, and an interface unit. The detection system comprises at least one sensor arrangement adapted to provide depth information of at least a part of an observed scene. The processing unit comprises a correlation unit adapted to correlate the depth information. The processing unit comprises a generation unit adapted to generate a 3D free space model. The interface unit is adapted to provide the 3D free space model.

The term "3D free space model" refers to spatial or volumetric data defining a space which is free of objects and structures and which can thus be used for movement, for example of a component or an element.

According to an exemplary embodiment of the invention, the detection system comprises at least one time-of-flight camera as sensor arrangement.

According to a further exemplary embodiment of the invention, a plurality of sensors is placed in such a way that objects can be seen by multiple sensors from multiple angles.

According to a second aspect of the invention, a medical examination system with motorized equipment is provided, comprising a motorized functional system and a medical safety-system according to one of the above described aspects or embodiments. The motorized functional system comprises a movable arrangement to perform at least one task. An adaptable movement restriction device is provided, which is adapted to restrict the movement of the arrangement to movements inside the 3D free space model provided by the interface unit.

According to an exemplary embodiment of the invention, the motorized functional system of the medical examination system is an image acquisition arrangement with a movable arrangement to acquire image data of an object from different projections. The image acquisition arrangement comprises a movable C-arm structure with an X-ray source and an X-ray detector arranged on opposing ends of the C-arm structure. The movement possibilities of the C-arm structure are limited to the 3D free space model.

According to a third aspect, a method for providing safe movements in dynamic 3D healthcare environments is provided, comprising the following steps: In a provision step, depth information of at least a part of an observed scene is provided. The depth information is correlated in a correlation step. A 3D free space model is generated in a generation step. In a second provision step, the 3D free space model is provided.

According to an exemplary embodiment of the invention, the 3D free space model is provided to a movable arrangement of a medical examination system with motorized equipment, and the movable arrangement can move freely within the 3D free space model. For example, movement is restricted to take place inside the volume defined by the 3D free space model.

According to a further exemplary embodiment of the invention, following the second provision step, a calculation step is provided, in which a movement path of a movable arrangement is calculated to be positioned inside the 3D free space model.

According to an embodiment of the invention, free space is detected and a 3D free space model is generated therefrom. The 3D free space model can then be used as the possible space in which a movement can be arranged. In particular, no external information about objects probably hindering a possible movement is needed, since the detection system only detects free space as such. The detection system is not coupled to any movable devices and therefore provides an improved adaptability in case of changes of the 3D healthcare environment. The generation of a 3D free space model also allows environments where movements are also influenced by external parameters, for example humanly controlled movements, and where the trajectories of a movable element are therefore not completely known beforehand.

These and other aspects of the present invention will become apparent from and elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
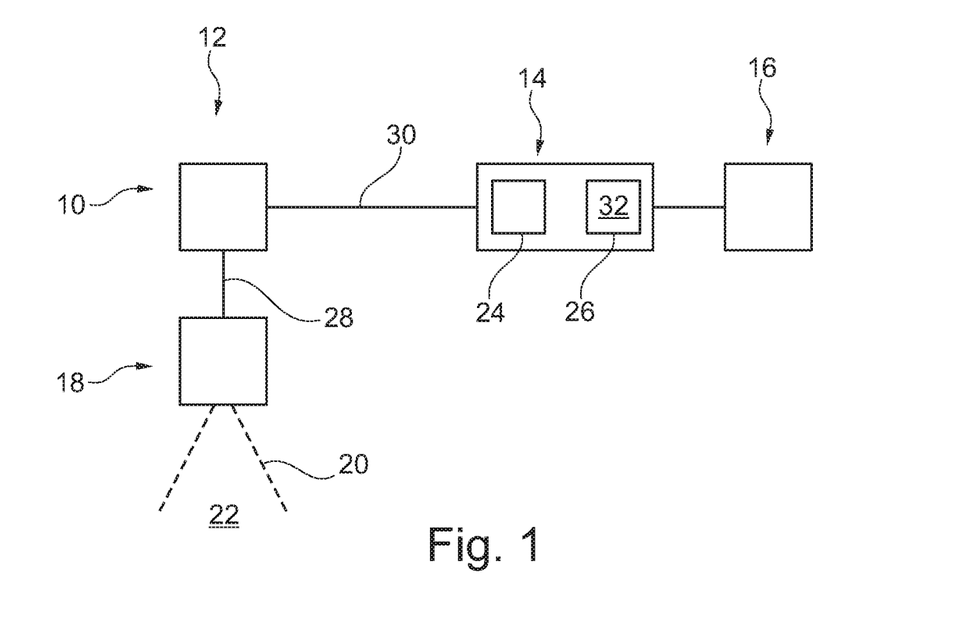
FIG. 1 illustrates a medical safety-system for dynamic 3D healthcare environments according to an exemplary embodiment of the present invention.

FIG. 1 shows a medical safety-system 10 for dynamic 3D healthcare environments. The medical safety-system 10 comprises a detection system 12, a processing unit 14, and an interface unit 16. The detection system 12 comprises at least one sensor arrangement 18 which is adapted to provide depth information of at least a part of an observed scene. In FIG. 1, the observation is schematically illustrated with two dotted lines 20 directed towards a reference numeral 22 representing the scene to be observed.

The processing unit 14 comprises a correlation unit 24 and a generation unit 26. The correlation unit 24 is adapted to correlate the depth information. The generation unit 26 is adapted to generate a 3D free space model 32.

Further, the interface unit 16 is adapted to provide the 3D free space model.

The at least one sensor arrangement 18 thus provides depth information to the detection system 12, indicated with a first connection line 28. The depth information is then provided to the processing unit, as indicated with second connection line 30. It must be noted that the connection lines are schematically shown, and can be provided as wireless connection or as wired connection.

The processing unit 14 is using the depth information in the correlation unit 24 and correlates depth information, for example a number of depth information from different space segments. The generation unit then generates the 3D free space model from the correlated depth information. The 3D free space model is schematically indicated with reference numeral 32 inside the box representing the generation unit 26.

It must be noted that the correlation unit 24 and the generation unit 26 are schematically shown and can be provided as separate computing units or as an integrated part of the processing unit 14. It must be noted further, that the detection system 12 and the at least one sensor arrangement 18 can also be provided as an integrated component, for example also integrated with the processing unit 14 into an integrated safety unit. Similar applies to the interface unit 16, which can also be provided in an integrated manner with the processing unit 14.

As indicated with the dotted lines 20, the sensor arrangement 18 provides information of a free space, i.e. a space without any material occupancy of any object, between the sensor and the detected depth.

For example, the correlation unit 24 reconstructs free space based on the depth information and the generation unit 26 merges the free space into the 3D free space model 32.

The 3D free space model comprises spatial or volumetric data defining a space which is free of objects and structures and which can thus be used for movement, for example of a component or an element (see below, for example FIGS. 5 to 8).

For example, in case of missing portions between detected depth information, the generation unit 26 can generate so-to-speak virtual depth data for the missing portions such that a complete volume is covered with free depth data to generate a 3D free space volume. For example, the missing portions can be achieved by interpolation. As a further example, in case of missing depth information, assumptions can be provided for certain space areas in which the arrangement of equipment must be expected and such areas where additional equipment is not provided with a high probability. For example, an area above table level and distinctly low enough below the ceiling will probably not show any further table arrangement or lighting arrangement.

For example, the at least one sensor or sensor arrangement is adapted to measure the free 3D depth structure of at least a part of a volume which is free for movement.

The environment may be an undefined or not predefined environment, such as in the case of an operation theatre of a hospital. An undefined or not predefined environment can also be any other situation in a healthcare environment, in which the current medical environment constantly changes in an unplanable and/or unpredictable manner.

The medical safety-system 10 is adapted to provide real-time 3D reconstruction of the free space available for movement in form of the 3D free space model 32.

Once a 3D free space model 32 has been generated, it is also possible to verify and update the depth information and to adapt the 3D free space model, for example by providing a respective update loop in the processing unit triggering the sensor to provide the respective update information and to provide a respectively updated 3D free space model to further processing steps, for example via the interface unit 16.

According to a further example, although not shown, the sensor is adapted to provide the depth information as temporal depth information and the generation unit 26 is adapted to provide a 4D free space model. Such, the interface unit can then provide the 4D free space model. For example, the sensor also provides a time signal coupled to the depth information such that the processing unit gets the information when the respective depth information is available.

For example, the temporal information can be used for repetitive movement cycles in the environment itself, for example due to other movable components.

Figure 2:
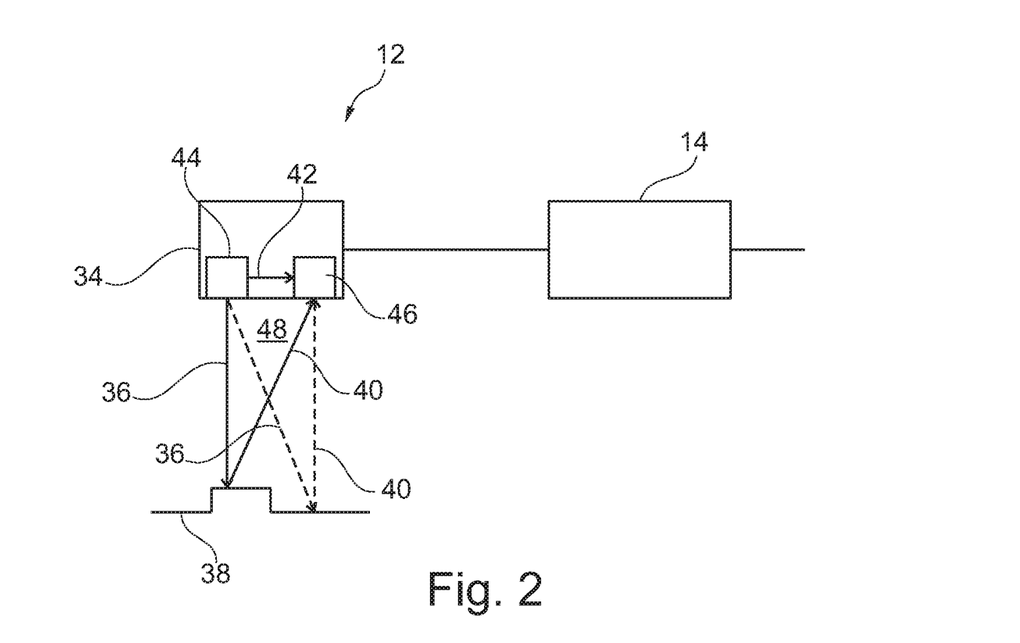
FIGS. 2 to 5 illustrate further examples of medical safety-systems according to the present invention.

In FIG. 2, a further example of the detection system 12 is shown. As can be seen, the detection system 12 comprises at least one time-of-flight camera 34 as sensor arrangement, which time-of-flight camera obtains and provides depth images. The depth images are then processed, for example, by a ray-tracing algorithm, where the space between the camera and the detected depth is declared as free space. With the cameras calibrated to the origin, these free spaces can be converted to a full free space model of the scene, as described above.

As a so-to-speak principle of a time-of-flight camera, it is indicated that the time-of-flight camera 34 emits modulated light 36 and measures the phase shift with its receiver as indicated with return arrows 40, which is reflected by object 38. A respective signal 42 is provided from the light emitting unit 44 to the light receiving unit 46. This is of course provided for a number of points in space, such that a respective free volume 48 between the time-of-flight camera 34 and the object 38 can be determined.

For example, the time-of-flight camera 34 uses infrared light.

The time-of-flight camera 34 is adapted to provide depth images and the processing unit 14 is adapted to combine a plurality of such depth images in order to be able to generate the 3D free space model 32 or the 4D free space model as mentioned above.

The processing unit 14 may be adapted to transfer the 3D free space model 32 to global space data of an examination laboratory, or a construction site or any other spatial situation, for example.

According to a further exemplary embodiment (not shown), the detection system 12 comprises at least one stereovision setup as sensor arrangement in order to provide the respective depth information.

According to a further exemplary embodiment (also not shown), the detection system 12 comprises at least one structured light setup as sensor arrangement.

According to a further exemplary embodiment (also not shown), the detection system 12 comprises at least one laser setup as sensor arrangement.

Figure 3:
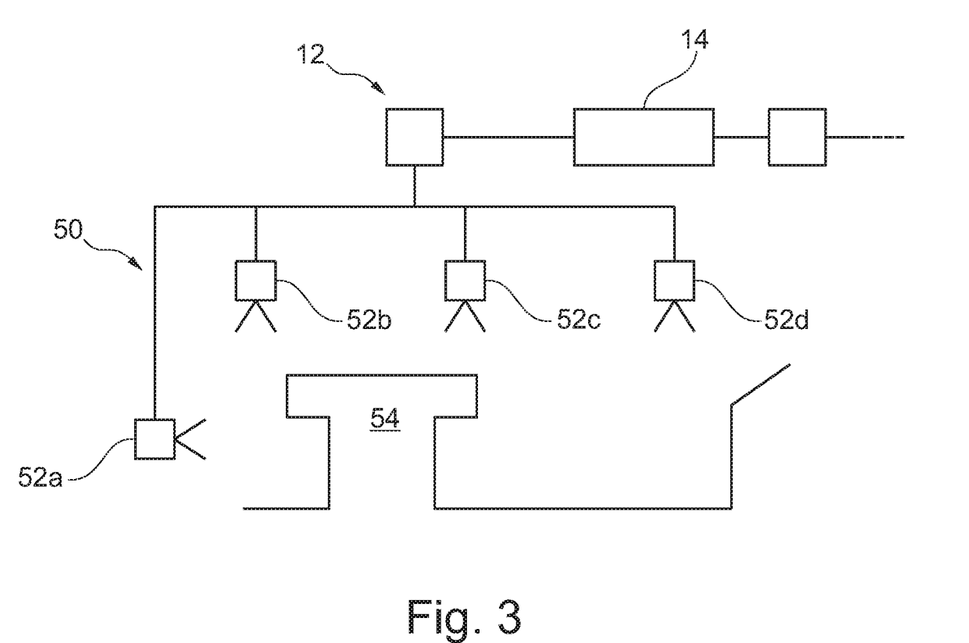

FIG. 3 shows a further exemplary embodiment, in which the detection system 12 comprises a plurality 50 of sensors 52 placed in such a way that objects can be seen by multiple sensors from multiple angles. For example, an object 54 is seen from the left side with sensor 52*a*, from the upper side with sensors 52*b* and 52*c*, and at least partially from the right side from sensor 52*d*.

For example, the sensors are provided as plurality of time-of-flight cameras that can be placed in such a way that objects can be seen by multiple cameras from multiple angles.

For example, the sensors are fixedly arranged and calibrated to their position in order to provide the respective depth data facilitating the generation of the 3D free space model by the processing unit 14.

The provision of a number of sensors provides the advantage that a 3D free space model can be calculated also for areas which would not have been detected as free space by a single sensor only, for example because they are arranged behind an object acting as a so-to-speak visual barrier.

Figure 4:
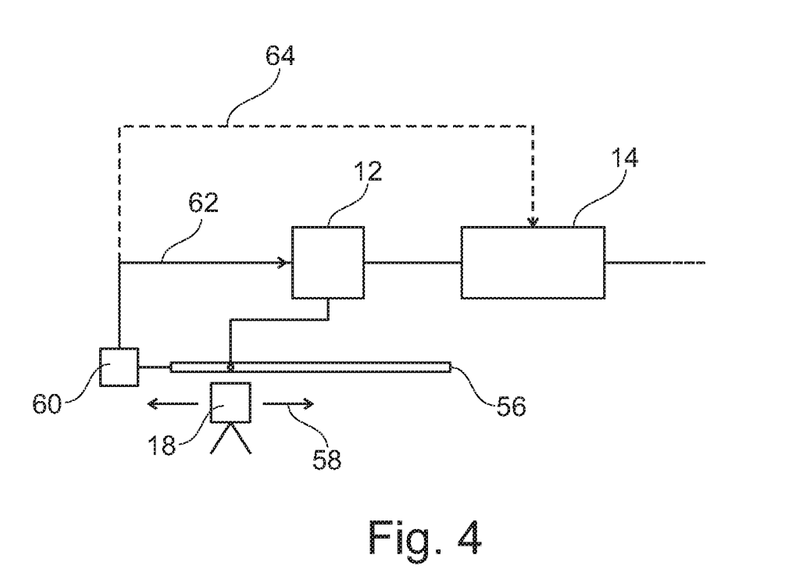

FIG. 4 shows a further exemplary embodiment of a medical safety-system wherein the sensors are movably mounted, for example on a rail construction 56. The movement possibility is indicated with arrows 58. Of course, the illustratively shown rail construction 56 is only an example. Of course, any other movable mounting supports, such as rotational movements or combination of movements, are also possible. For example, a sensor could be mounted to a ceiling or other upper structure with a number of movable wire constructions in order to cover a larger area of a volume arrangement underneath, i.e. to allow movement in the horizontal direction, as well as being able to be lowered to low heights in order to provide respective depth information also for areas hidden behind obstacles.

According to the exemplary embodiment shown in FIG. 4, the movement of the at least one sensor is detected, as indicated with a detection unit 60. The depth information provided by the sensor is then adjusted on behalf of the detected sensor position. This is indicated by an adjustment arrow 62 entering the detection system box 12. Of course, it is also possible to provide the respective movement information, as provided by the detection unit 60, to the processing unit 14, as indicated with dotted adjustment arrow 64. This provision of the movement information can be arranged alternatively or in addition to the adjustment arrow 62.

For example, at least a part of the area of reach of the moving apparatus is covered by at least one sensor.

For example, the whole area of reach of the moving apparatus is covered by a number of sensors.

For example, the moving apparatus is a motorized equipment, for example a C-arm in a medical examination system, which will be explained further below.

Figure 5:
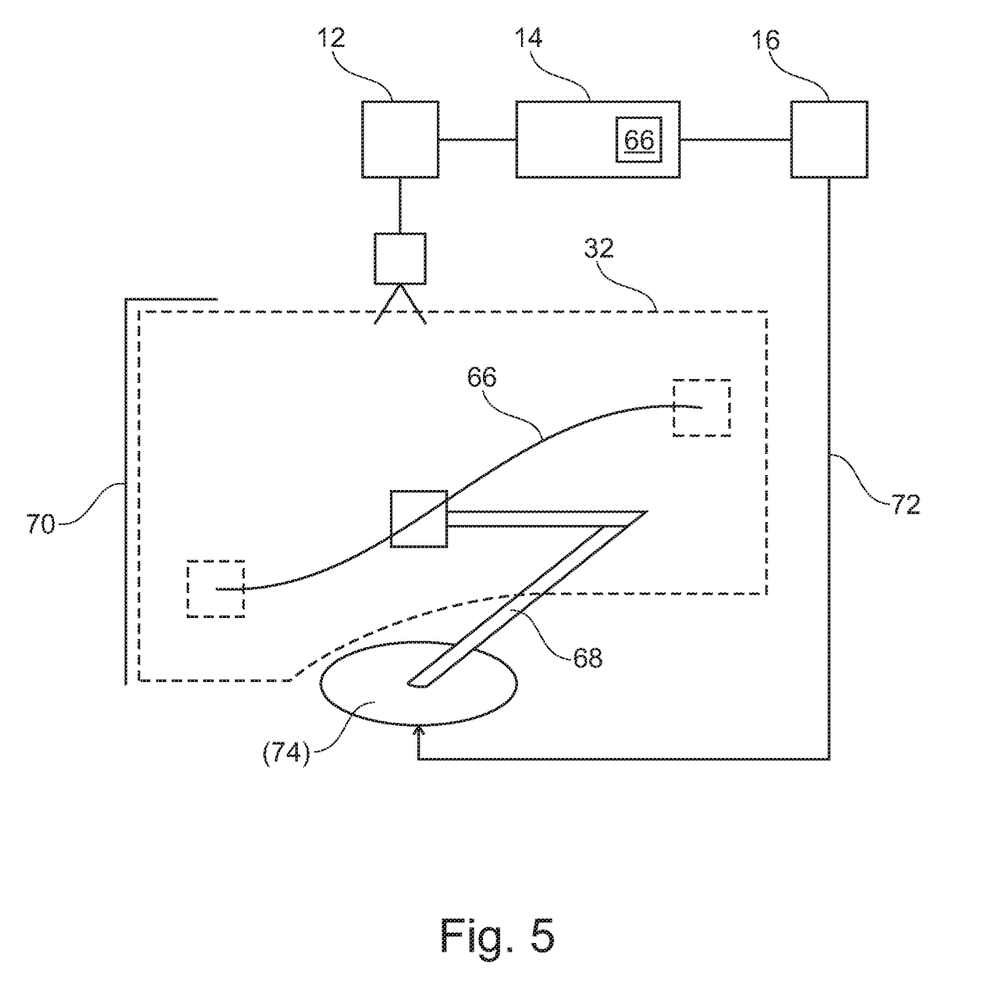

According to a further aspect of the invention, the processing unit 14 can also be adapted to calculate a movement path 66 for a moving apparatus 68, which movement path is located inside the 3D free space model 32 (see also FIG. 5).

With reference to FIG. 5, the moving apparatus 68 is only schematically illustrated in a very simplified manner. For example, the detection system 12 detects the dotted outer frame 32 as areas in which free space is available for movement such that this free space can be generated as the 3D free space model 32. Only schematically indicated is, for example, an object line 70 on the left side of the drawing.

However, it must be noted that according to the present invention, the object 70, for example, is not in particular necessary for defining the 3D free space model. It is rather only necessary to detect certain areas with depth information representing free volume in which a movement can take place. Thus, for example on the right side of the figure, a respective object corresponding to the one on the left side is not shown. However, free space was only detected up to the particular boundary of the 3D free space model, and thus the 3D free space model only extends across the shown area. However, this does not mean that a particular object is actually being arranged here, it just means that this is the actual space free for movement.

As an example, the interface unit 16 provides the respective information for the movement path 66 which is calculated by the processing unit 14 to the moving apparatus 68. It must be noted that the movement path 66 is provided in addition to the 3D free space model 32, which 3D free space model acts as a basis for the calculation of the movement path 66 itself. However, the 3D free space model 32 is not further shown in the calculation box as is the case in FIG. 1. The provision of the movement path 66 is indicated with an arrow 72. The restriction device is indicated with reference numeral 74, arranged in parentheses.

For example, the restriction device 74 can be provided as an actual adaptable hardware component restricting the movement of respective parts, and as such acting as limit stops or catches. However, the restriction device 74 can also be provided in form of an electronic control device limiting movement commands sent to the movement components such that the commands only result in movements inside the 3D free space model. This can also be provided in form of software, such as a plug-in module for an existing movement control software.

The 3D free space model can be provided to a movable arrangement, such as the moving apparatus 68, and an adaptable movement restriction device can be provided, which is not further shown, which restriction device is adapted to restrict the movement of the movable arrangement to movements inside the 3D free space model.

Figure 6:
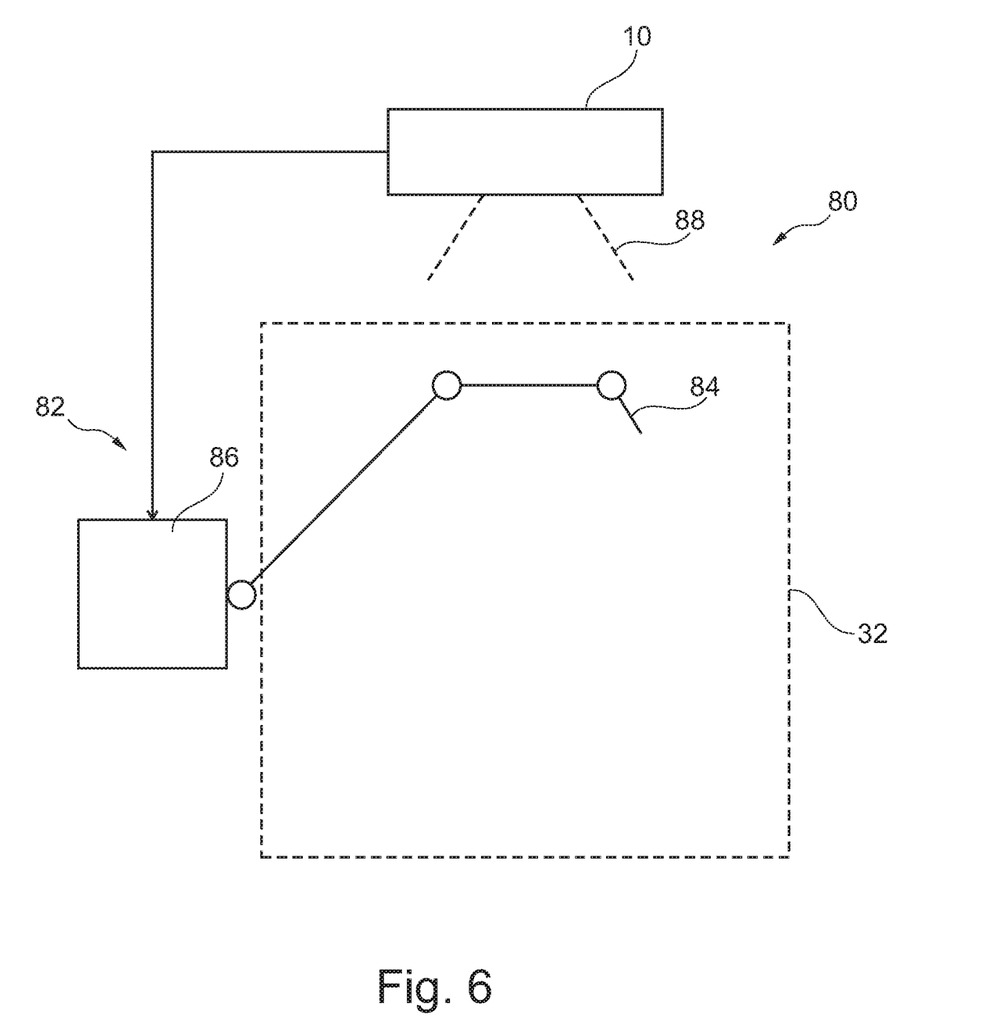
FIG. 6 illustrates a medical examination system with motorized equipment according to an exemplary embodiment of the present invention.

FIG. 6 schematically describes an exemplary embodiment of a medical examination system 80 with motorized equipment according to the invention. The medical examination system 80 comprised a motorized functional system 82, and a medical safety-system 10 according to one of the above described embodiments. The motorized functional system 82 comprises a movable arrangement 84 to perform at least one task. An adaptable movement restriction device 86 is provided (not further shown), which is adapted to restrict the movement of the arrangement to movements inside the 3D free space model provided by the medical safety-system 10. The motorized functional system is shown with a three segments' movable arm structure as an example for illustrational purposes only.

Further, the medical safety-system 10 is shown in a simplified manner with a rectangular box only and with two dotted lines 88 indicating the above described detection of depth information. It must be noted that the medical safety-system 10 can be provided as any of the above described examples, or in a combination of two or more of the above described examples.

The motorized functional system may be an image acquisition device with a movable arrangement to acquire image data of an object from different projections.

A medical examination system with motorized equipment can for example be a robot in a healthcare environment with unknown objects which may have unknown movements, too. Without the medical safety system according to the invention, this would mostly result in collisions.

As a further example, a medical system with motorized equipment can be a C-arm arrangement or C-arch in an operation theatre in relation with medical interventions. The C-arch can collide with other equipments or with the staff members, such as the doctors performing an operation.

According to the invention, a medical safety-system, for example using time-of-flight cameras, is provided to find the free space in which the robot or the C-arch can move.

Time-of-flight cameras can give depth information of the observed scene. By using multiple time-of-flight cameras in a scene and correlating the obtained depth information, the free space in the scene can be reconstructed, which finally can be converted into a 3D model of the free space. Using the information of the position of free spaces, movements with robotic arms or C-arches can be made in the observed scene, without colliding with any objects. Time-of-flight cameras also have the advantage that there is no limitation on the structure of the objects which surface is being detected, and they also work in real-time.

A further advantage is that the system according to the invention also provides a corporation between the moving equipment and the fixed equipment in relation with movable components of the system or motorized equipment, and also in relation with the user, moving in the scene. The movement of speed is also not limited, as is the case with, for example, capacitive and pressure sensors.

Providing the detection of the free spaces, and not the complete 3D environments in form of an object structure, limits also the amount of data necessary for detecting whether a path of a movable component is safe or not. Also, it is possible to start from a sort of centre point and to detect whether free space is available around this point. In case of a situation in which precise information, i.e. depth information is not available in a sufficient manner, i.e. with a sufficiently high probability, it is possible to simply neglect this space and to positively define the free space only for those area in which depth information positively defines that free space is actually available. Thus, in case of uncertainness, it is not necessary to make any assumptions, but rather to leave out this particular space to be on the safe side.

In case of using an infrared light for time-of-flight cameras, the system operates independently of light conditions. Further, since time-of-flight cameras are capable of capturing depth of at least 25 frames per second, it is possible to provide real-time 3D reconstruction.

A further advantage is that, according to the inventive system, no object information is needed; the system does in particular not need any information about the volume of an object.

An important advantage is that new objects can be introduced without any problems providing a general applicability.

Since the sensors can be freely arranged in the surrounding of the operation site, a large visible range with respect to detection of free space is provided. Therewith, path planning of larger path distances is possible, since the operation is not limited to a line of sight of a robot, for example. In case of the plurality of sensors, the system can look around objects and calculate a valid path even for those areas which, from the point of view of a robot, are not visible in the beginning of the path.

Figure 7:
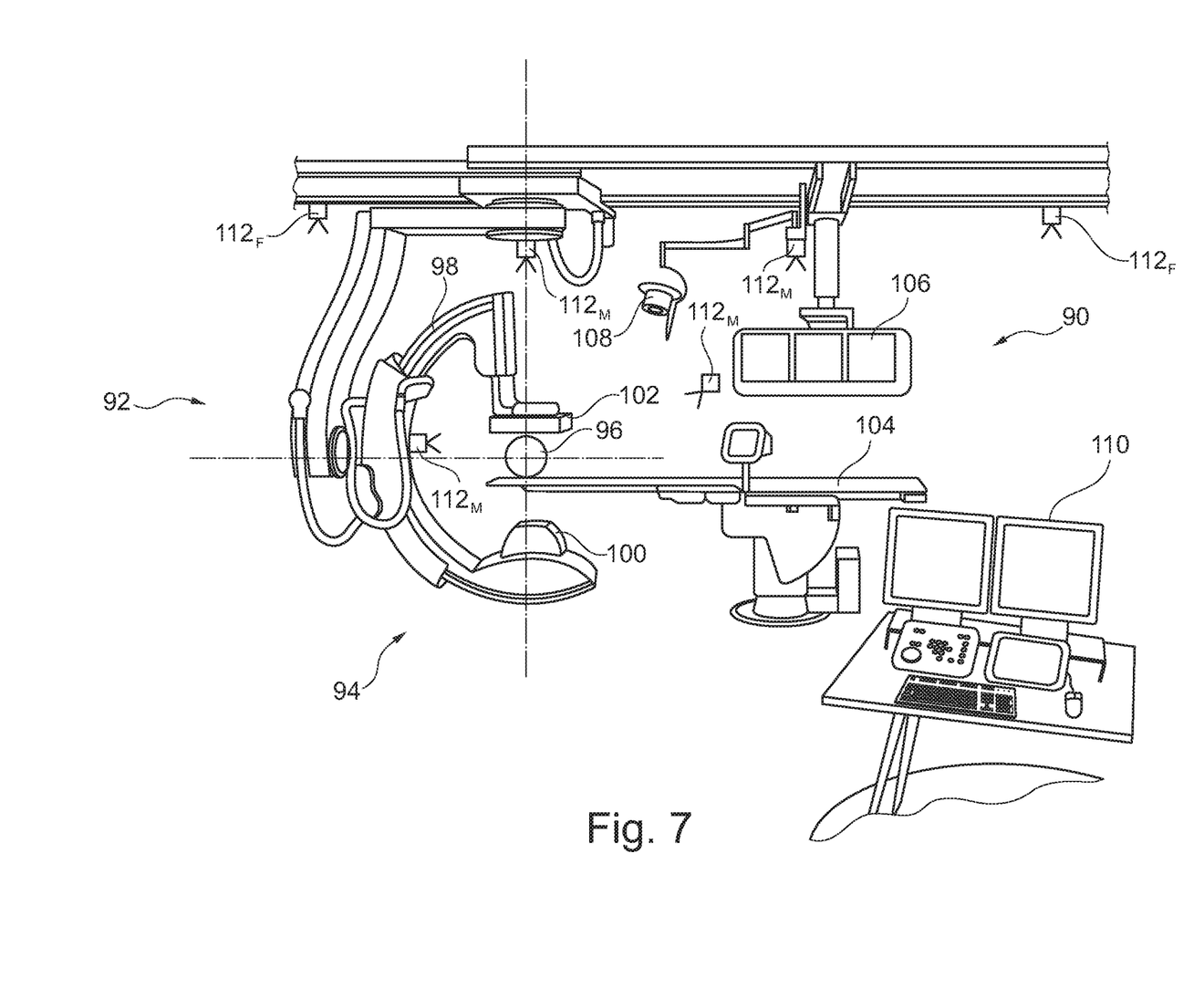
FIG. 7 illustrates a further example of a medical examination system with motorized equipment according to the present invention.

FIG. 7 shows an example for an examination system 90, for example for an operation theatre in a hospital. The motorized functional system is an image acquisition arrangement 92 with a movable arrangement 94 to acquire image data of an object 96, for example a patient, from different projections. The image acquisition arrangement 92 comprises a C-arm structure 98 with an X-ray source 100 and an X-ray detector 102 arranged on opposing ends of the C-arm structure. The movement possibilities of the C-arm structure are limited to the 3D free space model 32, which is not further shown in FIG. 7.

Further, a patient table 104 is shown to support the object of interest 96. Still further, a display arrangement 106 is shown in the vicinity of the table 104 as well as a lighting device 108. Further, a control station 110 is indicated in the foreground with displays and interface devices for controlling the examination system 90.

Further, a medical safety-system according to one of the above described examples is provided, of which only the sensors are shown as a plurality of sensors 112 arranged above and at the sides of the examination table 104. The sensors provide depth information of at least a part of the observed scene. The processing unit of the detection system can be provided in an integrated manner with the control station 110 of the examination system 90.

For example, a number of the sensors, indicated with index f is shown in a fixedly arranged manner at fixed points in the area of the ceiling. Further, movable detectors indicated with index m are provided, for example on moving parts such as the C-arm or the display arrangement. They also provide depth information, however in combination with their current situation in space, which is provided, for example, by position detection systems which are arranged anyway in order to provide information about the current status of the C-arm, or also the display arrangement.

Once the sensors have detected sufficient depth information, the 3D free space model is generated as described above and then supplied to the C-arm structure. Thus, the movement possibilities of the C-arm structure are limited to the 3D free space model in order to avoid collision of the C-arm structure with any of the above described components.

Due to the inventive medical safety-system, it is possible to arrange additional equipment in the vicinity of the table 104. Then, upon changing the equipment or other objects in the surrounding of the table, an update can be performed to achieve an updated 3D free space model. This can then be used for determining the movement paths of the C-arm structure for the image acquisition procedure.

The update can be provided continuously or with a predetermined time interval. The update can also be triggered manually.

With the position and orientation of a movable component, e.g. a robot, known in the environment, future movements of the component can be calculated.

The 3D free space model can be used, for example, for determining a movement path in space, such as when acquiring three-dimensional X-ray image information from a patient 96.

In addition to that, or alternatively, the 3D free space model can be used also for a free movement of the C-arm structure, for example by an operational staff, for example a surgeon, trying to find a specific view of a patient. Therefore, the user can control the movement of the C-arm structure in a free manner, however, the movement is then automatically restricted to the available space in form of the 3D free space model. Thus, the user is provided with a facilitated way of handling the C-arm, since it is no longer necessary to especially look for possible collision situations. Rather, the user can move the C-arm as he or she wants, since it is assured that a collision is avoided, due to limiting the movement possibilities to the generated 3D free space model.

It must be noted that the restriction of the movement possibilities can be provided, as mentioned above, in form of hardware components, actually limiting the movement, or in form of software means, restricting the respective movement commands to lie inside the 3D free space model.

As a further option, it is also possible to adapt a pre-calculated movement path of the C-arm structure, or any other imaging modality with movable components, such that the adaptive path then lies inside the 3D free space model. For example, this can be necessary in case of additional medical equipment, which has not been considered when computing the initial movement path.

It must be noted that any other collision warning systems, such as sensors, may not be necessary any more.

Figure 8:
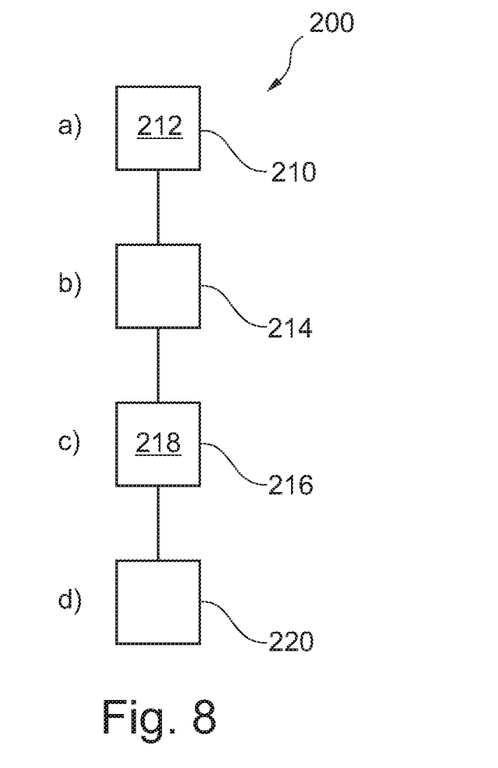
FIG. 8 schematically shows basic method steps of a method according to the present invention for providing safe movements in dynamic 3D healthcare environments.

FIG. 8 schematically describes a method 200 for providing safe movements in dynamic 3D healthcare environments. The following steps are provided: In a first provision step 210, depth information 212 of at least a part of an observed scene is provided. Next, in a correlation step 214, the depth information is correlated. Then, in a generation step 216, a 3D free space model 218 is generated. Further, in a second provision step 220, the 3D free space model 218 is provided. It is noted that above, the 3D free space model 218 has also been referred to with reference numeral 32.

Is must be noted that the first provision step 210 is also referred to as step a), the correlation step 214 as step b), the generation step 216 as step c), and the second provision step 220 as step d).

The 3D free space model 218 can be provided to a movable arrangement, and the movable arrangement can then move freely within the 3D free space model.

Figure 9:
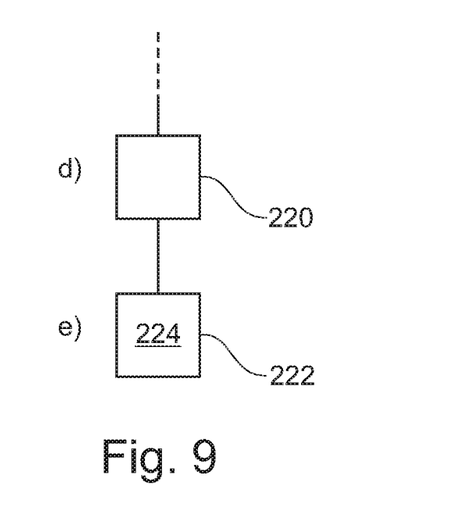
FIGS. 9 and 10 schematically illustrate further examples of methods according to the present invention.

According to the exemplary embodiment shown in FIG. 9, following step d), a step e) is provided as calculation step 222, in which a movement path 224 of a movable arrangement is calculated to be positioned inside the 3D free space model 218. The movement path 224 may be, for example, the movement path 66 in FIG. 5.

Figure 10:
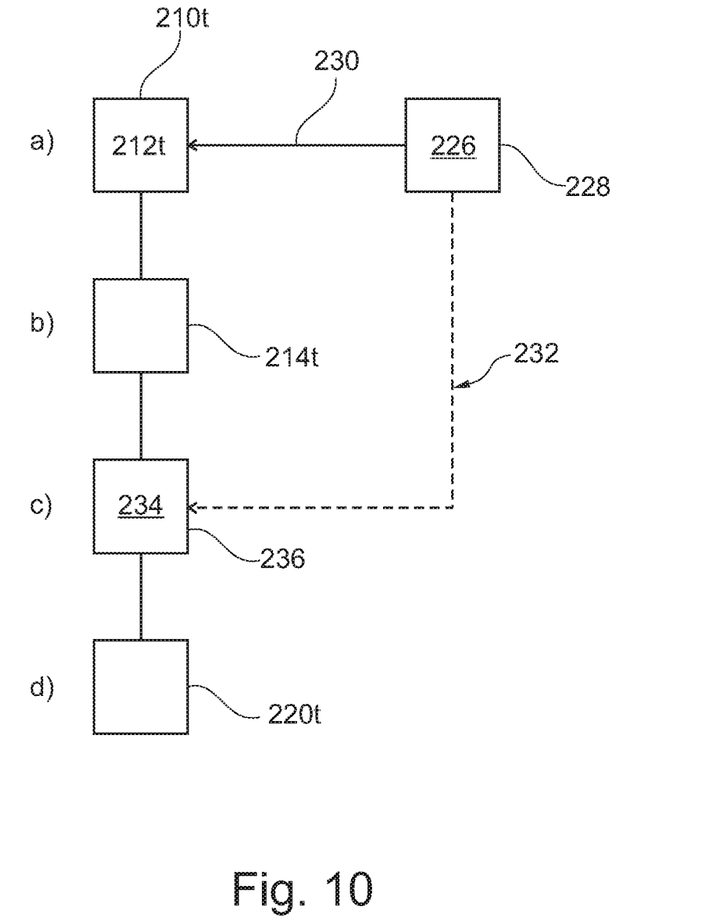

FIG. 10 shows a further exemplary embodiment of the method according to the invention, in which depth information is provided as temporal depth information 212*t*, wherein the provision step is indicated with reference numeral 210*t*. For example, a time signal 226 is provided by a time provision sub-step 228. For example, the time signal 226 can be provided directly to the first provision step 210*t*, as indicated with first provision arrow 230 in a straight line. However, it is also possible, in addition or alternatively, to provide the time signal 226 also to the generation step c), as indicated with dotted second provision arrow 232.

Thus, step b) comprises the correlation of the temporal depth information, which is why the correlation step is indicated with reference numeral 214*t*.

In step c), a 4D free space model 234 is generated, i.e. the step c) is a temporal generation step 236. The 4D free space model 234 is then provided in a provision step, referred to as provision step 220*t*.

It is noted that in case of providing the temporal information 226, or the time signal, only in step c), i.e. in the generation step 236, the above mentioned steps a) and b) are of course referred to as provision step 210 and correlation step 214, i.e. without the index t.

It must be noted that the above described exemplary embodiments of a method can be combined in different ways.

The term "healthcare" relates to all fields in which medical examination, medical treatment, medical intervention and the like are provided, for example in hospitals, doctor's practice etc. Healthcare relates also to diagnostic, as well as to the treatment and the prevention of injury, disease, or illness. The term "medical" defines the relation to the field of medicine.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A medical safety-system for controlling movement of a moveable object in a dynamic 3D healthcare environment, the medical safety-system comprising:
 a detection system comprising at least one sensor configured to capture depth information of an observed scene including depth information from a plurality of different space segments of the observed scene; and
 at least one processor configured to:
  determine free space in the observed scene based on correlation of the depth information of the observed scene, including the depth information from the plurality of different space segments of the observed scene, wherein the free space is space of the observed scene free of objects and structures and useable for movement of medical equipment,
  generate a 3D free space model based on the determined free space in the observed scene, wherein the 3D free space model defines a bounded movement area for moving the moveable object in the observed scene, and
  provide the generated 3D free space model to the moveable object to restrict movement of the moveable object to within the bounded movement area defined by the 3D free space model.

2. The medical safety-system according to claim 1, wherein the at least one sensor comprises at least one time-of-flight camera.

3. The medical safety-system according to claim 1, wherein the at least one sensor comprises a plurality of sensors that capture the observed scene from a plurality of angles.

4. The medical safety-system according to claim 1, wherein the at least one sensor is movably mounted, and the at least one processor is configured to detect a device position of each of the at least one sensor and adjust the depth information based on the device position.

5. The medical safety-system according to claim 1, wherein the at least one processor is further configured to calculate a movement path for moving the moveable object entirely within the bounded movement area defined by the 3D free space model.

6. The medical safety-system according to claim 1, wherein the at least one sensor and the at least one processor are external to the moveable object, wherein the observed scene includes the moveable object, and wherein the at least one processor is further configured to generate the 3D free space model based on positions of objects and structures in the observed scene detected by the at least one sensor.

7. The medical safety-system according to claim 6, wherein the at least one processor is further configured to update the 3D free space model based on movement of the moveable object in the observed scene detected by the at least one sensor.

8. The medical safety-system according to claim 1, wherein the 3D free space model includes only data corresponding to space free of objects and structures in the observed scene.

9. The medical safety-system according to claim 1, further comprising:
 an image acquisition system configured to acquire image data of an imaged object from different projections, the image acquisition system comprising a movable C-arm structure as the moveable object, and an X-ray source and an X-ray detector arranged on opposing ends of the C-arm structure; and
 a movement restriction device configured to restrict movement of the C-arm structure to within the bounded movement area defined by the 3D free space model.

10. The medical safety-system according to claim 1, wherein the moveable object is moveable medical equipment.

11. The medical safety-system according to claim 1, wherein, to determine the free space of the observed scene, the at least one processor is further configured to generate virtual depth data for a portion of a volume of the observed scene missing from the captured depth information.

12. The medical safety-system according to claim 1, wherein, to reconstruct the free space of the observed scene, the at least one processor is further configured to predict free space in a portion of the observed scene missing from the captured depth information.

13. A method for providing safe movement of a moveable object in a dynamic 3D healthcare environment, the method comprising:
    capturing depth information of an observed scene, including depth information from a plurality of different space segments of the observed scene;
    determining free space in the observed scene based on correlating the depth information of the observed scene, including the depth information from the plurality of different space segments of the observed scene, wherein the free space is space of the observed scene free of objects and structures and useable for movement of medical equipment;
    generating a 3D free space model based on the determined free space in the observed scene, wherein the 3D free space model defines a bounded movement area for moving the moveable object in the observed scene; and
    providing the generated 3D free space model to the moveable object for restricting movement of the moveable object to within the bounded movement area defined by the 3D free space model.

14. The method according to claim 13, further comprising calculating a movement path for the moveable object entirely within the bounded movement area defined by the 3D free space model.

15. The method according to claim 13, wherein the depth information is captured by at least one sensor that is external to the moveable object, wherein the observed scene includes the moveable object, and further comprising generating the 3D free space model based on positions of objects and structures in the observed scene in captured images.

16. The method according to claim 15, further comprising updating the 3D free space model based on movement of the moveable object in the observed scene.

17. The method according to claim 13, wherein the 3D free space model includes only data corresponding to space free of objects and structures in the observed scene.

18. The method according to claim 13, wherein the depth information comprises temporal depth information, and the method further comprises generating and providing a 4D free space model.

19. The method according to claim 13, wherein the moveable object is moveable medical equipment.

20. A non-transitory computer readable medium having stored thereon a program for controlling movement of a moveable object in a medical environment, the program comprising instructions which, when executed by a processor, cause the processor to:
    receive depth information of an observed scene, including depth information from a plurality of different space segments of the observed scene;
    determine free space in the observed scene based on correlation of the depth information of the observed scene, including the depth information from the plurality of different space segments of the observed scene, wherein the free space is space of the observed scene free of objects and structures and useable for movement of medical equipment;
    generate a 3D free space model based on the determined free space in the observed scene, wherein the 3D free space model defines a bounded movement area for moving the moveable object in the observed scene; and
    provide the generated 3D free space model to the moveable object to restrict movement of the moveable object to within the bounded movement area defined by the 3D free space model.

21. The non-transitory computer readable medium according to claim 20, wherein the instructions, when executed by the processor, further cause the processor to calculate a movement path for the moveable object entirely within the bounded movement area defined by the 3D free space model.

22. The non-transitory computer readable medium according to claim 20, wherein the processor is separate from the moveable object, wherein the observed scene includes the moveable object, and wherein the instructions, when executed by the processor, further cause the processor to generate the 3D free space model based on positions of objects and structures in the observed scene.

* * * * *